(12) United States Patent
Bumbalough

(10) Patent No.: US 9,603,703 B2
(45) Date of Patent: *Mar. 28, 2017

(54) INTRAOCULAR LENS AND METHODS FOR PROVIDING ACCOMMODATIVE VISION

(71) Applicant: Abbott Medical Optics Inc., Santa Ana, CA (US)

(72) Inventor: Timothy R Bumbalough, Fullerton, CA (US)

(73) Assignee: ABBOTT MEDICAL OPTICS INC., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,595

(22) Filed: Dec. 21, 2012

(65) Prior Publication Data

US 2013/0166026 A1 Jun. 27, 2013

Related U.S. Application Data

(63) Continuation of application No. 12/849,451, filed on Aug. 3, 2010, now Pat. No. 8,343,217.

(Continued)

(51) Int. Cl.
*A61F 2/16* (2006.01)

(52) U.S. Cl.
CPC .............. *A61F 2/1624* (2013.01); *A61F 2/16* (2013.01); *A61F 2/1613* (2013.01); *A61F 2002/1681* (2013.01)

(58) Field of Classification Search
CPC .. A61F 2002/1681; A61F 2/16; A61F 2/1613; A61F 2/1648; A61F 2/1629; A61F 2/1635; A61F 2/1624

(Continued)

(56) References Cited

U.S. PATENT DOCUMENTS 1,483,509 A 2/1924 Bugbee
2,129,305 A 9/1938 William
(Continued)

FOREIGN PATENT DOCUMENTS

AU 3225789 A1 10/1989
CH 681687 A5 5/1993
(Continued)

OTHER PUBLICATIONS

English translation of WO93/05733A1.
(Continued)

*Primary Examiner* — Howie Matthews
(74) *Attorney, Agent, or Firm* — Abbott Medical Optics Inc.

(57) ABSTRACT

An accommodating intraocular lens for providing a range of accommodative vision contains an optic and a haptic. The optic is disposed about an optical axis and includes an anterior surface and a posterior surface defining a clear aperture of the optic. The haptic is at least partially disposed inside the optic and includes an inner structure, an outer structure, and a plurality of arms disposed between and connecting the inner structure and the outer structure. The inner structure is circumferentially disposed about the optical axis, while the outer structure is circumferentially disposed about the inner structure and has an outer face. Each arm has proximal portion adjacent the inner structure and a distal portion adjacent the outer structure that is bifurcated in a radial direction from the proximal portion. The intraocular lens also has an outer surface defined by outer surfaces of the plurality of arms and an outer surface of the outer structure. The inner structure and at least a portion of the arms are disposed inside the clear aperture. The distal portion of each arm has a larger axial extent than an axial extent of the inner portion. The distal portion of each arm (Continued)

has a larger axial extent along the outer surface than an axial extent of the outer structure along the outer surface.

6 Claims, 6 Drawing Sheets

Related U.S. Application Data

(60) Provisional application No. 61/230,914, filed on Aug. 3, 2009.

(58) Field of Classification Search
USPC .......... 623/6.11, 6.37–6.43, 6.46, 6.49, 6.51, 623/6.16, 6.17, 6.19
See application file for complete search history.

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley |
| 3,222,432 A | 12/1965 | Grandperret |
| 3,227,507 A | 1/1966 | William |
| 3,305,294 A | 2/1967 | Alvarez |
| 3,339,997 A | 9/1967 | Wesley |
| 3,415,597 A | 12/1968 | Willard |
| 3,420,006 A | 1/1969 | Howard |
| 3,431,327 A | 3/1969 | George |
| 3,482,906 A | 12/1969 | David |
| 3,507,565 A | 4/1970 | Luis et al. |
| 3,542,461 A | 11/1970 | Louis et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |

(56) References Cited

U.S. PATENT DOCUMENTS

| | | | |
|---|---|---|---|
| 4,664,666 | A | 5/1987 | Barrett |
| 4,666,444 | A | 5/1987 | Pannu |
| 4,666,445 | A | 5/1987 | Tillay |
| 4,676,792 | A | 6/1987 | Praeger |
| 4,676,793 | A | 6/1987 | Bechert, II |
| 4,687,484 | A | 8/1987 | Kaplan |
| 4,693,572 | A | 9/1987 | Tsuetaki et al. |
| 4,693,716 | A | 9/1987 | Mackool |
| RE32,525 | E | 10/1987 | Pannu |
| 4,702,244 | A | 10/1987 | Mazzocco |
| 4,704,016 | A | 11/1987 | De Carle |
| 4,710,193 | A | 12/1987 | Volk |
| 4,710,194 | A | 12/1987 | Kelman |
| 4,711,638 | A | 12/1987 | Lindstrom |
| 4,720,286 | A | 1/1988 | Bailey et al. |
| 4,725,278 | A | 2/1988 | Shearing |
| 4,731,078 | A | 3/1988 | Stoy et al. |
| 4,737,322 | A | 4/1988 | Bruns et al. |
| 4,752,123 | A | 6/1988 | Blaker |
| 4,759,762 | A | 7/1988 | Grendahl |
| 4,769,033 | A | 9/1988 | Nordan |
| 4,769,035 | A | 9/1988 | Kelman |
| 4,780,154 | A | 10/1988 | Mori et al. |
| 4,787,903 | A | 11/1988 | Grendahl |
| 4,790,847 | A | 12/1988 | Woods |
| 4,808,170 | A | 2/1989 | Thornton et al. |
| 4,813,955 | A | 3/1989 | Achatz et al. |
| 4,816,030 | A | 3/1989 | Robinson |
| 4,816,031 | A | 3/1989 | Pfoff |
| 4,816,032 | A | 3/1989 | Hetland |
| 4,822,360 | A | 4/1989 | Deacon |
| 4,828,558 | A | 5/1989 | Kelman |
| 4,830,481 | A | 5/1989 | Futhey et al. |
| 4,834,749 | A | 5/1989 | Orlosky |
| 4,840,627 | A | 6/1989 | Blumenthal |
| 4,842,601 | A | 6/1989 | Smith |
| 4,865,601 | A | 9/1989 | Caldwell et al. |
| 4,878,910 | A | 11/1989 | Koziol et al. |
| 4,878,911 | A | 11/1989 | Anis |
| 4,880,427 | A | 11/1989 | Anis |
| 4,881,804 | A | 11/1989 | Cohen |
| 4,883,485 | A | 11/1989 | Patel |
| 4,888,012 | A | 12/1989 | Horn et al. |
| 4,888,014 | A | 12/1989 | Nguyen |
| 4,888,015 | A | 12/1989 | Domino |
| 4,888,016 | A | 12/1989 | Langerman |
| 4,890,912 | A | 1/1990 | Visser |
| 4,890,913 | A | 1/1990 | De Carle |
| 4,892,543 | A | 1/1990 | Turley |
| 4,898,416 | A | 2/1990 | Hubbard et al. |
| 4,898,461 | A | 2/1990 | Portney |
| 4,902,293 | A | 2/1990 | Feaster |
| 4,906,246 | A | 3/1990 | Grendahl |
| 4,917,681 | A | 4/1990 | Nordan |
| 4,919,663 | A | 4/1990 | Grendahl |
| 4,921,496 | A | 5/1990 | Grendahl |
| 4,923,296 | A | 5/1990 | Erickson |
| 4,929,289 | A | 5/1990 | Moriya et al. |
| 4,932,966 | A | 6/1990 | Christie et al. |
| 4,932,968 | A | 6/1990 | Caldwell et al. |
| 4,932,971 | A | 6/1990 | Kelman |
| 4,938,583 | A | 7/1990 | Miller |
| 4,946,469 | A | 8/1990 | Sarfarazi |
| 4,955,902 | A | 9/1990 | Kelman |
| 4,961,746 | A | 10/1990 | Lim et al. |
| 4,963,148 | A | 10/1990 | Sulc et al. |
| 4,976,534 | A | 12/1990 | Miege et al. |
| 4,976,732 | A | 12/1990 | Vorosmarthy |
| 4,990,159 | A | 2/1991 | Kraff |
| 4,994,058 | A | 2/1991 | Raven et al. |
| 4,994,082 | A | 2/1991 | Richards et al. |
| 4,994,083 | A | 2/1991 | Sulc et al. |
| 4,995,880 | A | 2/1991 | Galib |
| 4,997,442 | A | 3/1991 | Barrett |
| 5,000,559 | A | 3/1991 | Takahashi et al. |
| 5,002,382 | A | 3/1991 | Seidner |
| 5,002,571 | A | 3/1991 | O'Donnell et al. |
| 5,018,504 | A | 5/1991 | Terbrugge et al. |
| 5,019,098 | A | 5/1991 | Mercier |
| 5,019,099 | A | 5/1991 | Nordan |
| 5,026,396 | A | 6/1991 | Darin |
| 5,044,742 | A | 9/1991 | Cohen |
| 5,047,051 | A | 9/1991 | Cumming |
| 5,047,052 | A | 9/1991 | Dubroff |
| 5,054,905 | A | 10/1991 | Cohen |
| 5,056,908 | A | 10/1991 | Cohen |
| 5,066,301 | A | 11/1991 | Wiley |
| 5,071,432 | A | 12/1991 | Baikoff |
| 5,074,877 | A | 12/1991 | Nordan |
| 5,074,942 | A | 12/1991 | Kearns et al. |
| 5,078,740 | A | 1/1992 | Walman |
| 5,089,024 | A | 2/1992 | Christie et al. |
| 5,096,285 | A | 3/1992 | Silberman |
| 5,108,429 | A | 4/1992 | Wiley |
| 5,112,351 | A | 5/1992 | Christie et al. |
| 5,117,306 | A | 5/1992 | Cohen |
| 5,123,921 | A | 6/1992 | Werblin et al. |
| 5,129,718 | A | 7/1992 | Futhey et al. |
| 5,133,748 | A | 7/1992 | Feaster |
| 5,133,749 | A | 7/1992 | Nordan |
| 5,141,507 | A | 8/1992 | Parekh |
| 5,147,397 | A | 9/1992 | Christ et al. |
| 5,152,788 | A | 10/1992 | Isaacson et al. |
| 5,152,789 | A | 10/1992 | Willis |
| 5,158,572 | A | 10/1992 | Nielsen |
| 5,166,711 | A | 11/1992 | Portney |
| 5,166,712 | A | 11/1992 | Portney |
| 5,166,719 | A | 11/1992 | Chinzei et al. |
| 5,171,266 | A | 12/1992 | Wiley et al. |
| 5,171,267 | A | 12/1992 | Ratner et al. |
| 5,171,320 | A | 12/1992 | Nishi |
| 5,172,723 | A | 12/1992 | Sturgis |
| 5,173,723 | A | 12/1992 | Volk |
| 5,180,390 | A | 1/1993 | Drews |
| 5,192,317 | A | 3/1993 | Kalb |
| 5,192,318 | A | 3/1993 | Schneider et al. |
| 5,196,026 | A | 3/1993 | Barrett et al. |
| 5,197,981 | A | 3/1993 | Southard |
| 5,201,762 | A | 4/1993 | Hauber |
| 5,203,788 | A | 4/1993 | Wiley |
| 5,213,579 | A | 5/1993 | Yamada et al. |
| 5,217,491 | A | 6/1993 | Vanderbilt |
| 5,225,858 | A | 7/1993 | Portney |
| 5,229,797 | A | 7/1993 | Futhey et al. |
| 5,236,452 | A | 8/1993 | Nordan |
| 5,236,970 | A | 8/1993 | Christ et al. |
| 5,258,025 | A | 11/1993 | Fedorov et al. |
| 5,260,727 | A | 11/1993 | Oksman et al. |
| 5,270,744 | A | 12/1993 | Portney |
| 5,275,623 | A | 1/1994 | Sarfarazi |
| 5,275,624 | A | 1/1994 | Hara et al. |
| 5,296,881 | A | 3/1994 | Freeman |
| 5,326,347 | A | 7/1994 | Cumming |
| 5,336,261 | A | 8/1994 | Barrett et al. |
| 5,344,448 | A | 9/1994 | Schneider et al. |
| 5,349,394 | A | 9/1994 | Freeman et al. |
| 5,354,335 | A | 10/1994 | Lipshitz et al. |
| 5,358,520 | A | 10/1994 | Patel |
| 5,366,499 | A | 11/1994 | Py |
| 5,366,502 | A | 11/1994 | Patel |
| 5,376,694 | A | 12/1994 | Christ et al. |
| 5,391,202 | A | 2/1995 | Lipshitz et al. |
| 5,405,386 | A | 4/1995 | Rheinish et al. |
| 5,408,281 | A | 4/1995 | Zhang |
| 5,423,929 | A | 6/1995 | Doyle et al. |
| RE34,988 | E | 7/1995 | Yang et al. |
| RE34,998 | E | 7/1995 | Langerman |
| 5,443,506 | A | 8/1995 | Garabet |
| 5,476,445 | A | 12/1995 | Baerveldt et al. |
| 5,476,514 | A | 12/1995 | Cumming |
| 5,480,428 | A | 1/1996 | Fedorov et al. |
| 5,489,301 | A | 2/1996 | Barber |
| 5,489,302 | A | 2/1996 | Skottun |
| 5,494,946 | A | 2/1996 | Christ et al. |

(56) References Cited

U.S. PATENT DOCUMENTS

| | | |
|---|---|---|
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,608,471 A | 3/1997 | Miller |
| 5,609,630 A | 3/1997 | Crozafon |
| 5,628,795 A | 5/1997 | Langerman |
| 5,628,796 A | 5/1997 | Suzuki |
| 5,628,797 A | 5/1997 | Richer |
| 5,650,837 A | 7/1997 | Roffman et al. |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,661,195 A | 8/1997 | Christ et al. |
| 5,674,282 A | 10/1997 | Cumming |
| 5,682,223 A | 10/1997 | Menezes et al. |
| 5,684,560 A | 11/1997 | Roffman et al. |
| 5,695,509 A | 12/1997 | El Hage |
| 5,702,440 A | 12/1997 | Portney |
| 5,713,958 A | 2/1998 | Weiser |
| 5,716,403 A | 2/1998 | Tran et al. |
| 5,725,576 A | 3/1998 | Fedorov et al. |
| 5,728,155 A | 3/1998 | Anello et al. |
| 5,760,871 A | 6/1998 | Kosoburd et al. |
| 5,766,244 A | 6/1998 | Binder |
| 5,769,890 A | 6/1998 | McDonald |
| 5,770,125 A | 6/1998 | O'Connor et al. |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,864,378 A | 1/1999 | Portney |
| 5,869,549 A | 2/1999 | Christ et al. |
| RE36,150 E | 3/1999 | Gupta |
| 5,876,441 A | 3/1999 | Shibuya |
| 5,876,442 A | 3/1999 | Lipshitz et al. |
| 5,885,279 A | 3/1999 | Bretton |
| 5,895,422 A | 4/1999 | Hauber |
| 5,898,473 A | 4/1999 | Seidner et al. |
| 5,928,283 A | 7/1999 | Gross et al. |
| 5,929,969 A | 7/1999 | Roffman |
| 5,968,094 A | 10/1999 | Werblin et al. |
| 5,984,962 A | 11/1999 | Anello et al. |
| 6,013,101 A | 1/2000 | Israel |
| 6,015,435 A | 1/2000 | Valunin et al. |
| 6,050,970 A | 4/2000 | Baerveldt |
| 6,051,024 A | 4/2000 | Cumming |
| 6,063,118 A | 5/2000 | Nagamoto |
| 6,083,261 A | 7/2000 | Callahan et al. |
| 6,090,141 A | 7/2000 | Lindstrom |
| 6,096,078 A | 8/2000 | McDonald |
| 6,102,946 A | 8/2000 | Nigam |
| 6,106,553 A | 8/2000 | Feingold |
| 6,106,554 A | 8/2000 | Bretton |
| 6,110,202 A | 8/2000 | Barraquer et al. |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,152,958 A | 11/2000 | Nordan |
| 6,162,249 A | 12/2000 | Deacon et al. |
| 6,176,878 B1 | 1/2001 | Gwon et al. |
| 6,186,148 B1 | 2/2001 | Okada |
| 6,197,058 B1 | 3/2001 | Portney |
| 6,197,059 B1 | 3/2001 | Cumming |
| 6,200,342 B1 | 3/2001 | Tassignon |
| 6,210,005 B1 | 4/2001 | Portney |
| 6,217,612 B1 | 4/2001 | Woods |
| 6,221,105 B1 | 4/2001 | Portney |
| 6,224,628 B1 | 5/2001 | Callahan et al. |
| 6,228,115 B1 | 5/2001 | Hoffmann et al. |
| 6,231,603 B1 | 5/2001 | Lang et al. |
| 6,238,433 B1 | 5/2001 | Portney |
| 6,241,777 B1 | 6/2001 | Kellan |
| 6,251,312 B1 | 6/2001 | Phan et al. |
| 6,258,123 B1 | 7/2001 | Young et al. |
| 6,261,321 B1 | 7/2001 | Kellan |
| 6,277,146 B1 | 8/2001 | Peyman et al. |
| 6,277,147 B1 | 8/2001 | Christ et al. |
| 6,280,471 B1 | 8/2001 | Peyman et al. |
| 6,299,641 B1 | 10/2001 | Woods |
| 6,302,911 B1 | 10/2001 | Hanna |
| 6,322,213 B1 | 11/2001 | Altieri et al. |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,364,906 B1 | 4/2002 | Baikoff et al. |
| 6,387,126 B1 | 5/2002 | Cumming |
| 6,399,734 B1 | 6/2002 | Hodd et al. |
| 6,406,494 B1 | 6/2002 | Laguette et al. |
| 6,423,094 B1 | 7/2002 | Sarfarazi |
| 6,425,917 B1 | 7/2002 | Blake |
| 6,443,985 B1 | 9/2002 | Woods |
| 6,450,642 B1 | 9/2002 | Jethmalani et al. |
| 6,454,802 B1 | 9/2002 | Bretton et al. |
| 6,457,826 B1 | 10/2002 | Lett |
| 6,464,725 B2 | 10/2002 | Skotton et al. |
| 6,468,306 B1 | 10/2002 | Paul et al. |
| 6,474,814 B1 | 11/2002 | Griffin |
| 6,475,240 B1 | 11/2002 | Paul |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,533,813 B1 | 3/2003 | Lin et al. |
| 6,533,814 B1 | 3/2003 | Jansen |
| 6,536,899 B1 | 3/2003 | Fiala |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,589,550 B1 | 7/2003 | Hodd et al. |
| 6,592,621 B1 | 7/2003 | Domino |
| 6,598,606 B2 | 7/2003 | Terwee et al. |
| 6,599,317 B1 | 7/2003 | Weinschenk, III |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III |
| 6,660,035 B1 | 12/2003 | Lang et al. |
| 6,685,315 B1 | 2/2004 | De Carle |
| 6,695,881 B2 | 2/2004 | Peng et al. |
| 6,721,104 B2 | 4/2004 | Schachar et al. |
| 6,730,123 B1 | 5/2004 | Klopotek |
| 6,749,633 B1 | 6/2004 | Lorenzo et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,827,738 B2 | 12/2004 | Willis et al. |
| 6,846,326 B2 | 1/2005 | Zadno-Azizi et al. |
| 6,855,164 B2 | 2/2005 | Glazier |
| 6,858,040 B2 | 2/2005 | Nguyen et al. |
| 6,884,261 B2 | 4/2005 | Zadno-Azizi et al. |
| 6,884,262 B2 | 4/2005 | Brady et al. |

(56) References Cited

U.S. PATENT DOCUMENTS

| | | |
|---|---|---|
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 6,930,838 B2 | 8/2005 | Schachar |
| 6,942,695 B1 | 9/2005 | Chapoy et al. |
| 7,018,409 B2 | 3/2006 | Glick et al. |
| 7,021,760 B2 | 4/2006 | Newman |
| 7,025,783 B2 | 4/2006 | Brady et al. |
| 7,041,134 B2 | 5/2006 | Nguyen et al. |
| 7,073,906 B1 | 7/2006 | Portney |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,150,759 B2 | 12/2006 | Paul et al. |
| 7,179,292 B2 | 2/2007 | Worst et al. |
| 7,182,780 B2 | 2/2007 | Terwee et al. |
| 7,186,266 B2 | 3/2007 | Peyman |
| 7,188,949 B2 | 3/2007 | Bandhauer et al. |
| 7,198,640 B2 | 4/2007 | Nguyen |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,247,168 B2 | 7/2007 | Esch et al. |
| 7,261,737 B2 | 8/2007 | Esch et al. |
| 7,344,617 B2 | 3/2008 | Dubrow |
| 7,452,362 B2 | 11/2008 | Zadno-Azizi et al. |
| 7,452,378 B2 | 11/2008 | Zadno-Azizi et al. |
| 7,503,938 B2 | 3/2009 | Phillips |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 7,815,678 B2 | 10/2010 | Ben Nun |
| 7,922,326 B2 | 4/2011 | Bandhauer et al. |
| 8,034,108 B2 | 10/2011 | Bumbalough |
| 8,052,752 B2 | 11/2011 | Woods et al. |
| 2001/0001836 A1 | 5/2001 | Cumming |
| 2001/0004708 A1 | 6/2001 | Nagai |
| 2001/0018612 A1 | 8/2001 | Carson et al. |
| 2001/0039451 A1 | 11/2001 | Barnett |
| 2001/0044657 A1 | 11/2001 | Kellan |
| 2002/0004682 A1 | 1/2002 | Zhou et al. |
| 2002/0011167 A1 | 1/2002 | Figov et al. |
| 2002/0072796 A1 | 6/2002 | Hoffmann et al. |
| 2002/0103536 A1 | 8/2002 | Landreville et al. |
| 2002/0120329 A1 | 8/2002 | Lang et al. |
| 2002/0151973 A1 | 10/2002 | Arita et al. |
| 2002/0161434 A1 | 10/2002 | Laguette et al. |
| 2002/0193876 A1 | 12/2002 | Lang et al. |
| 2003/0002404 A1 | 1/2003 | Maekawa |
| 2003/0004569 A1 | 1/2003 | Haefliger |
| 2003/0013073 A1 | 1/2003 | Duncan et al. |
| 2003/0020425 A1 | 1/2003 | Ricotti |
| 2003/0033013 A1 | 2/2003 | Callahan et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0086057 A1 | 5/2003 | Cleveland |
| 2003/0105522 A1 | 6/2003 | Glazier |
| 2003/0109925 A1 | 6/2003 | Ghazizadeh et al. |
| 2003/0114927 A1 | 6/2003 | Nagamoto |
| 2003/0130732 A1 | 7/2003 | Sarfarazi |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2004/0002757 A1 | 1/2004 | Lai et al. |
| 2004/0010496 A1 | 1/2004 | Behrendt et al. |
| 2004/0014049 A1 | 1/2004 | Cowsert et al. |
| 2004/0015236 A1 | 1/2004 | Sarfarazi |
| 2004/0034415 A1 | 2/2004 | Terwee et al. |
| 2004/0039446 A1 | 2/2004 | McNicholas |
| 2004/0082993 A1 | 4/2004 | Woods |
| 2004/0082995 A1 | 4/2004 | Woods |
| 2004/0106992 A1 | 6/2004 | Lang et al. |
| 2004/0111153 A1 | 6/2004 | Woods et al. |
| 2004/0117013 A1 | 6/2004 | Schachar |
| 2004/0148023 A1 | 7/2004 | Shu |
| 2004/0156014 A1 | 8/2004 | Piers et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2004/0230299 A1 | 11/2004 | Simpson et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0018504 A1 | 1/2005 | Marinelli et al. |
| 2005/0021139 A1 | 1/2005 | Shadduck |
| 2005/0021140 A1 | 1/2005 | Liao |
| 2005/0027354 A1 | 2/2005 | Brady et al. |
| 2005/0038510 A1 | 2/2005 | Portney et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0099597 A1 | 5/2005 | Sandstedt et al. |
| 2005/0125056 A1 | 6/2005 | Deacon et al. |
| 2005/0125057 A1 | 6/2005 | Cumming |
| 2005/0125058 A1 | 6/2005 | Cumming et al. |
| 2005/0125059 A1 | 6/2005 | Pinchuk et al. |
| 2005/0131535 A1 | 6/2005 | Woods |
| 2005/0137703 A1 | 6/2005 | Chen |
| 2005/0234547 A1 | 10/2005 | Nguyen et al. |
| 2005/0246019 A1 | 11/2005 | Blake et al. |
| 2005/0267575 A1 | 12/2005 | Nguyen et al. |
| 2005/0288785 A1 | 12/2005 | Portney et al. |
| 2006/0030938 A1 | 2/2006 | Altmann |
| 2006/0064162 A1 | 3/2006 | Klima |
| 2006/0095127 A1 | 5/2006 | Feingold et al. |
| 2006/0098162 A1 | 5/2006 | Bandhauer et al. |
| 2006/0100703 A1 | 5/2006 | Evans et al. |
| 2006/0111776 A1 | 5/2006 | Glick et al. |
| 2006/0116764 A1 | 6/2006 | Simpson |
| 2006/0116765 A1 | 6/2006 | Blake et al. |
| 2006/0178741 A1 | 8/2006 | Zadno-Azizi et al. |
| 2006/0184244 A1 | 8/2006 | Nguyen et al. |
| 2006/0209430 A1 | 9/2006 | Spivey |
| 2006/0209431 A1 | 9/2006 | Spivey |
| 2006/0238702 A1 | 10/2006 | Glick et al. |
| 2006/0259139 A1 | 11/2006 | Zadno-Azizi et al. |
| 2006/0271187 A1 | 11/2006 | Zadno-Azizi et al. |
| 2007/0032866 A1 | 2/2007 | Portney |
| 2007/0050025 A1 | 3/2007 | Nguyen et al. |
| 2007/0067872 A1 | 3/2007 | Mittendorf et al. |
| 2007/0078515 A1 | 4/2007 | Brady |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106379 A1 | 5/2007 | Messner |
| 2007/0106381 A1 | 5/2007 | Blake |
| 2007/0108643 A1 | 5/2007 | Zadno-Azizi et al. |
| 2007/0123591 A1 | 5/2007 | Kuppuswamy et al. |
| 2007/0129798 A1 | 6/2007 | Chawdhary |
| 2007/0135915 A1 | 6/2007 | Klima |
| 2007/0156236 A1 | 7/2007 | Stenger |
| 2007/0213817 A1 | 9/2007 | Esch et al. |
| 2007/0258143 A1 | 11/2007 | Portney |
| 2007/0260309 A1 | 11/2007 | Richardson |
| 2007/0282247 A1 | 12/2007 | Desai et al. |
| 2007/0299487 A1 | 12/2007 | Shadduck |
| 2008/0004699 A1 | 1/2008 | Ben Nun |
| 2008/0125790 A1 | 5/2008 | Tsai et al. |
| 2008/0140192 A1 | 6/2008 | Humayun et al. |

(56) References Cited

U.S. PATENT DOCUMENTS

| | | |
|---|---|---|
| 2008/0161913 A1 | 7/2008 | Brady et al. |
| 2008/0161914 A1 | 7/2008 | Brady et al. |
| 2008/0300680 A1 | 12/2008 | Joshua |
| 2009/0012609 A1 | 1/2009 | Geraghty et al. |
| 2009/0234448 A1 | 9/2009 | Weeber et al. |
| 2010/0057203 A1 | 3/2010 | Glick et al. |
| 2010/0228346 A1 | 9/2010 | Esch |
| 2011/035001 A1 | 2/2011 | Woods |
| 2012/0046744 A1 | 2/2012 | Woods et al. |

FOREIGN PATENT DOCUMENTS

| | | |
|---|---|---|
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 162573 A2 | 11/1985 |
| EP | 212616 A2 | 3/1987 |
| EP | 246216 A2 | 11/1987 |
| EP | 328117 A2 | 8/1989 |
| EP | 329981 A1 | 8/1989 |
| EP | 331457 A2 | 9/1989 |
| EP | 336877 A1 | 10/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 766540 A1 | 4/1997 |
| EP | 779063 A1 | 6/1997 |
| EP | 780718 A1 | 6/1997 |
| EP | 897702 A2 | 2/1999 |
| EP | 766540 B1 | 8/1999 |
| EP | 1108402 A2 | 6/2001 |
| EP | 1321112 A1 | 6/2003 |
| EP | 1647241 A2 | 4/2006 |
| EP | 1424049 B1 | 6/2009 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | 2126847 A | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 8404449 A1 | 11/1984 |
| WO | 8603961 A1 | 7/1986 |
| WO | 8700299 A1 | 1/1987 |
| WO | 8707496 A1 | 12/1987 |
| WO | 8803961 A1 | 6/1988 |
| WO | 8902251 A1 | 3/1989 |
| WO | 8911672 A1 | 11/1989 |
| WO | 8911872 A1 | 12/1989 |
| WO | 9000889 A1 | 2/1990 |
| WO | 9109336 A1 | 6/1991 |
| WO | 9302639 A1 | 2/1993 |
| WO | 9416648 A1 | 8/1994 |
| WO | 9503783 A1 | 2/1995 |
| WO | 9610968 A1 | 4/1996 |
| WO | 9615734 A2 | 5/1996 |
| WO | 9625126 A1 | 8/1996 |
| WO | 9635398 A1 | 11/1996 |
| WO | 9712272 A1 | 4/1997 |
| WO | 9727825 A1 | 8/1997 |
| WO | 9743984 A1 | 11/1997 |
| WO | 9805273 A1 | 2/1998 |
| WO | 9821621 A1 | 5/1998 |
| WO | 9849594 A1 | 11/1998 |
| WO | 9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | 0027315 A1 | 5/2000 |
| WO | 0035379 A1 | 6/2000 |
| WO | 0046629 A1 | 8/2000 |
| WO | 0059407 A1 | 10/2000 |
| WO | 0061036 A1 | 10/2000 |
| WO | 0066037 A1 | 11/2000 |
| WO | 0066039 A1 | 11/2000 |
| WO | 0066040 A1 | 11/2000 |
| WO | 0066041 A1 | 11/2000 |
| WO | 0108605 A1 | 2/2001 |
| WO | 0119288 A1 | 3/2001 |
| WO | 0119289 A1 | 3/2001 |
| WO | 0128144 A1 | 4/2001 |
| WO | 0134061 A1 | 5/2001 |
| WO | 0134066 A1 | 5/2001 |
| WO | 0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | 0219949 A2 | 3/2002 |
| WO | 0258391 A2 | 7/2002 |
| WO | 0271983 A1 | 9/2002 |
| WO | 02098328 A1 | 12/2002 |
| WO | 03009051 A2 | 1/2003 |
| WO | 03015657 A2 | 2/2003 |
| WO | 03015669 A1 | 2/2003 |
| WO | 03034949 A2 | 5/2003 |
| WO | 03049646 A2 | 6/2003 |
| WO | 03057081 A2 | 7/2003 |
| WO | 03059196 A2 | 7/2003 |
| WO | 03059208 A2 | 7/2003 |
| WO | 03075810 A1 | 9/2003 |
| WO | 03084441 A1 | 10/2003 |

(56) References Cited

FOREIGN PATENT DOCUMENTS

| | | |
|---|---|---|
| WO | 03092552 A1 | 11/2003 |
| WO | 2004000171 A1 | 12/2003 |
| WO | 2004020549 A1 | 3/2004 |
| WO | 2004037127 A2 | 5/2004 |
| WO | 2004073559 A1 | 9/2004 |
| WO | 2005011531 A2 | 2/2005 |
| WO | 2005018504 A1 | 3/2005 |
| WO | 2005019871 A2 | 3/2005 |
| WO | 03082147 A3 | 8/2005 |
| WO | 2005084587 A2 | 9/2005 |
| WO | 2005115278 A1 | 12/2005 |
| WO | 2006025726 A1 | 3/2006 |
| WO | 2006118452 A1 | 11/2006 |
| WO | 2007040964 A1 | 4/2007 |
| WO | 2007067872 A2 | 6/2007 |
| WO | 2008077795 A2 | 7/2008 |
| WO | 2008079671 A1 | 7/2008 |
| WO | 2008108524 A1 | 9/2008 |
| WO | 2009021327 A1 | 2/2009 |
| WO | 2010093823 A2 | 8/2010 |
| ZA | 8808414 A | 7/1989 |

OTHER PUBLICATIONS

U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.
Adler-Grinberg D., "Questioning Our Classical Understanding of Accommodation and Presbyopia," American Journal of Optometry & Physiological Optics, 1986, vol. 63 (7), pp. 571-580.
Altan-Yaycioglu R., et al., "Pseudo-accommodation with Intraocular Lenses Implanted in the Bag," Journal of Refractive Surgery, 2002, vol. 18 (3), pp. 271-275.
Amo Specs Model AC-21B, AMO Classic Series, 1992, 1 page.
Chiron, Clemente Optfit Model SP525, Brochure Translation, Jul. 12, 1998.
Chrion Vision, Nuvita MA20, 1997, 1 page.
Cohen A.L., "Diffractive Bifocal Lens Design," Optometry and Vision Science, 1993, vol. 70 (6), pp. 461-468.
Cohen A.L., "Practical Design of a Bifocal Hologram Contact Lens or Intraocular Lens," Applied Optics, 1992, vol. 31(19), pp. 3750-3754.
Fechner P.U., et al., "Iris-Claw Lens in Phakic Eyes to Correct Hyperopia: Preliminary Study," Journal of Cataract and Refractive Surgery, 1998, vol. 24 (1), pp. 48-56.
Foldable Intraocular Lens Implants and Small Incision Cataract Surgery, Ohio Valley Eye Physicians, 2004.
Hara T., et al., "Accommodative Intraocular Lens with Spring Action Part 1 Design and Placement in an Excised Animal Eye," Ophthalmic Surgery, 1990, vol. 21 (2), pp. 128-133.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
International Search Report for Application No. PCT/US2010/044248, mailed on Nov. 4, 2010, 4 pages.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70 (6), pp. 139-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracomeal Lenses," International Ophthalmology Clinics, 1991, vol. 31 (1), pp. 37-46.
Mandell R.B., "Contact Lens Practice", 4th Edition, Charles C. Thomas Publishers, 1988, 11 pages.
Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, 1990, vol. 1211, pp. 62-66.
McCarey B.E., et al., "Modeling Glucose Distribution in the Cornea," Current Eye Research, 1990, vol. 9 (11), pp. 1025-1039.
Menezo J.L., et al., "Endothelial Study of Iris-Claw Phakic Lens: Four Year Follow-Up," Journal of Cataract Refractive Surgery, 1998, vol. 24 (8), pp. 1039-1049.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Simonov A.N., et al., "Cubic Optical Elements for an Accommodative Intraocular Lens," Optics Express, 2006, vol. 14 (17), pp. 7757-7775.
Supplementary European Search Report for Application No. EP00980998, mailed on Sep. 11, 2007, 2 pages.
Supplementary European Search Report for Application No. EP02748257, mailed on Jun. 23, 2008, 2 pages.
Supplementary European Search Report for Application No. EP03777934, mailed on Jan. 26, 2010, 3 pages.
Supplementary European Search Report for Application No. EP03809651, mailed on Aug. 11, 2006, 2 pages.
Supplementary European Search Report for Application No. EP04814069, mailed on Jul. 12, 2007, 1 page.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Video presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
World Optics Inc., Ophthalmology Times, Mar. 15, 1995.

INTRAOCULAR LENS AND METHODS FOR PROVIDING ACCOMMODATIVE VISION

CLAIM OF PRIORITY

This application is a continuation application and claims priority to U.S. application Ser. No. 12/849,451, entitled "Intraocular Lens and Methods for Providing Accommodative Vision", filed on Aug. 3, 2010, and now U.S. Pat. No. 8,343,217 which claims priority under 35 U.S.C §119(e) to provisional application No. 61/230,914, filed on Aug. 3, 2009 under the same title, the entire contents of both of which are hereby incorporated by reference in their entirety for all purposes as if fully set forth herein.

BACKGROUND OF THE INVENTION

Field of the Invention

The present invention relates generally to intraocular lenses, and more specifically to intraocular lenses for providing accommodative vision to a human or animal subject.

Description of the Related Art

A human eye can suffer diseases that impair a person's vision. For instance, a cataract may increase the opacity of the lens, causing impaired vision or blindness. To restore the patient's vision, the diseased lens may be surgically removed and replaced with an artificial lens, known as an intraocular lens (IOL). An IOL may also be used for presbyopic lens exchange.

The simplest IOLs have a single fixed focal length, or, equivalently, a single fixed power. Unlike the eye's natural lens, which can adjust its focal length and/or axial location within a particular range in a process known as accommodation, these single focal length IOLs cannot generally accommodate. As a result, distant objects may appear in focus, while objects at closer distances appear blurred.

An improvement over fixed, single focal length IOLs is an accommodating IOL (AIOL), which can move axially and/or adjust its optical power within a particular range. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "distant" or "far" power. When the eye focuses on a relatively close object, the lens power and/or position is at the high end of the accommodation range, which may be referred to as the "near" power. The accommodation range or add power, as used herein, is defined as the actual or effective near power provided by a lens or optic (e.g., the natural lens or the optic of an IOL) minus the far power provided by the lens or optic. In general, an accommodation range of 2 to 4 Diopters is considered sufficient for most patients.

The human eye contains a structure known as the capsular bag, which surrounds the natural lens. The capsular bag is transparent, and serves to hold the lens. In the natural eye, accommodation is initiated by the ciliary muscle and a series of connective fibers known as zonules. The zonules are located in a relatively thick band mostly around the equator of the lens, and impart a largely radial force to the capsular bag that can alter the shape and/or the location of the natural lens and thereby change its actual or effective power.

In a surgery in which the natural lens is removed from the eye, a small opening is typically made in the front of the capsular bag through which lens material is typically broken up and vacuumed out of the eye, the rest of the capsular bag being left intact. The remaining capsular bag may be extremely useful for an accommodating intraocular lens, in that the eye's natural accommodation is initiated at least in part by an ocular force produced by the ciliary muscle, zonules, and/or capsular bag. The capsular bag may be used to house an accommodating IOL, which in turn can change shape or optical power of the IOL, and/or shift or axially move the optic of the IOL in some manner to affect the location of the image plane of the optic.

In general, the IOL includes an optic, which refracts and/or diffracts light that passes through it and forms an image on the retina, and a haptic or support structure, which mechanically couples the optic to the capsular bag. During accommodation, the zonules exert a force on the capsular bag, which in turn exerts a force on the optic. The force may be transmitted from the capsular bag directly to the optic, or from the capsular bag through a haptic to the optic.

A desirable optic for an accommodating IOL is one that changes shape or axially moves in response to an ocular force produced by a squeezing or expanding radial force applied largely to the equator of the optic (e.g., by pushing or pulling on or near the edge of the optic, circumferentially around the optic axis). Under the influence of an ocular force, the optic may bulge slightly in the axial direction, producing more steeply curved anterior and/or posterior faces, and produce an increase in the power of the optic. Likewise, an expanding radial force may produce a decrease in the optic power by flattening the optic. This change in power is accomplished in a manner similar to that of the natural eye.

One challenge in providing an effective AIOL is that of effectively transferring a limited amount of ocular force available from the ciliary muscle or capsular bag of an eye to the optic of the AIOL. Typically, the available ocular force is transferred through a haptic or support structure that absorbs a certain amount of the available energy provided by the ocular force. There is a need to provide haptic or support structures in AIOLs that reduce the amount of energy transferred to that structure so that more of the available force may be converted to changing the shape and/or axial position of the optic portion of the AIOL.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

Figure 1:
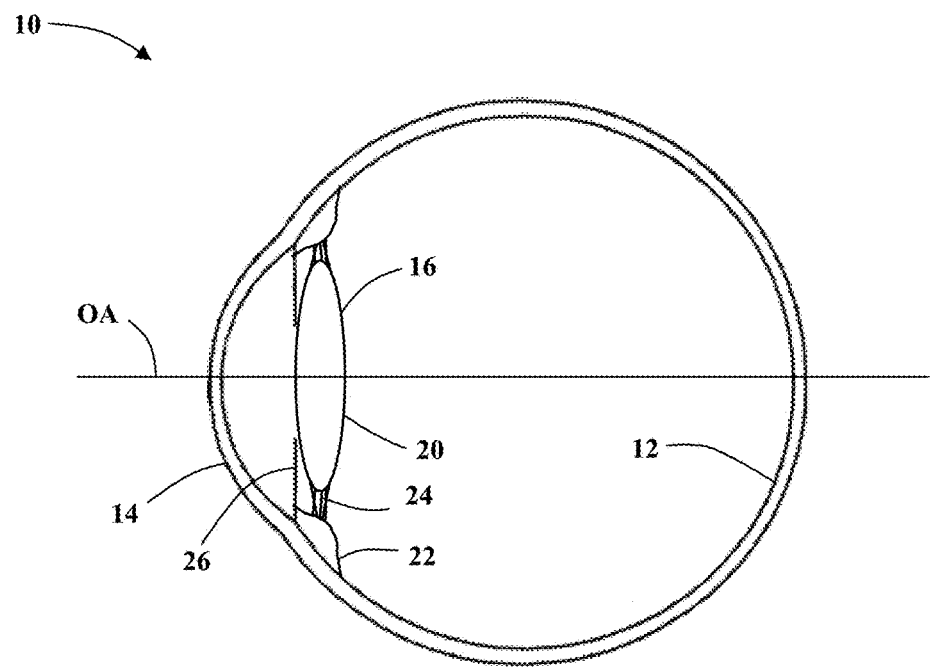
FIG. 1 is a plan drawing of a human eye with a natural lens.

Referring to FIG. 1, an eye 10 is illustrated that includes a retina 12 for receiving an image produced by a cornea 14 and a natural lens 16 from light incident upon eye 10. Natural lens 16 is disposed within a capsular bag 20 which separates anterior and posterior chambers of eye 10. Capsular bag 20 is made of a resilient material that changes the shape and/or location of natural lens 16 in response to ocular forces produced when ciliary muscle 22 contracts and stretches natural lens 16 via zonules 24 disposed about an equatorial region of capsular bag 20. This action flattens natural lens 16, thereby producing a relatively low optical power for providing distant vision in an emmetropic eye. To produce intermediate and/or near vision, ciliary muscle 22 relaxes, thereby relieving tension on zonules 24. The resiliency of capsular bag 20 provides an ocular force that reshapes natural lens 16 to increase its curvature and provide a relatively high optical power suitable for intermediate and/or near vision.

Figure 2:
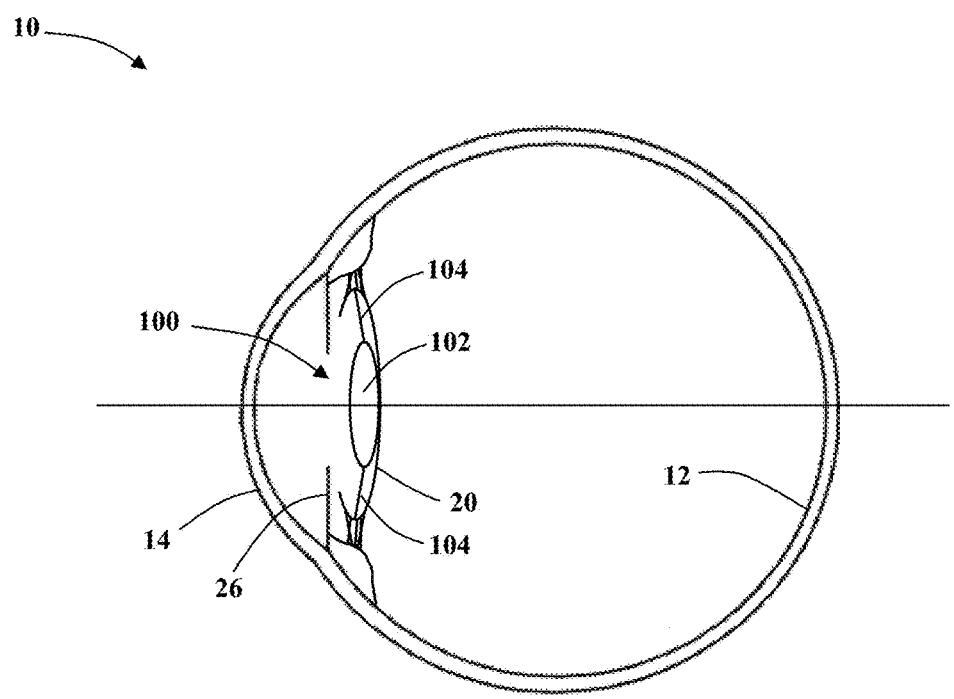
FIG. 2 is a plan drawing of a human eye with an intraocular lens.
Figure 3:
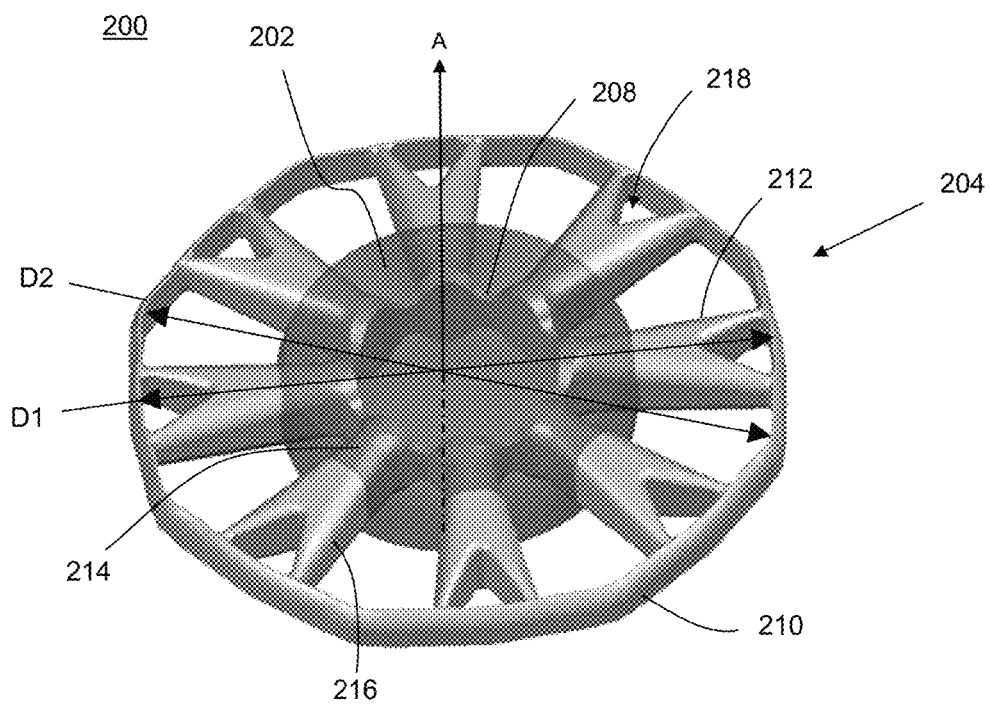
FIG. 3 is a perspective view of an intraocular lens embodying features of this invention.
Figure 4:
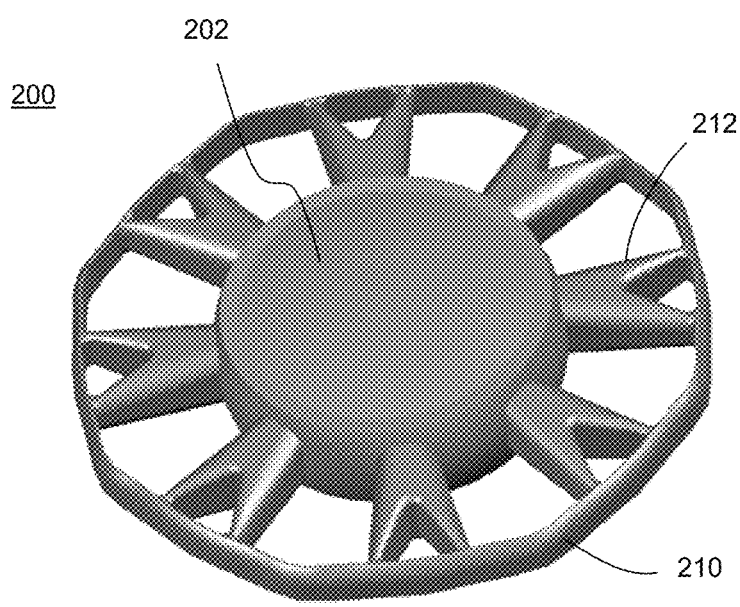
FIG. 4 is a perspective view of an intraocular lens embodying features of this invention.

Referring to FIG. 2, natural lens 16 may be removed either in a refractive lens exchange or due to a disease such as cataracts. Natural lens 16 is generally removed via an opening in the anterior wall of the capsular bag 20 (a so called "capsulorhexis"). Natural lens 16 may then be replaced by an IOL or AIOL 100 to provide vision to the subject. IOL 100 includes optic 102 for forming an image on the retina and haptics or support structure 104 for centering optic 102 and, in the case of an AIOL, transferring ocular forces from ciliary muscle 22, zonules 24, and/or capsular bag 20 to optic 102 to changes its shape, power, and/or axial location relative to the retina 12.

Referring to FIGS. 3-6, an AIOL 200 according to an embodiment of the present invention is shown disposed about an optical axis A. AIOL 200 comprises an optic 202 and a haptic or support structure 204 configured to effectively transfer an ocular force from a human or animal eye to the optic 202 so as to produce a range of powers in response to the ocular force. Haptic 204 includes an inner structure 208 and outer structure 210 and a plurality of arms 212 connecting or coupling structures 208, 210 to one another in a way that efficiently and effectively transfers ocular forces. Haptic 204 thus changes the shape and/or axial location of the optic 202, thereby providing a change in optic power and/or focal plane location of optic 202. Arms 212 each include a proximal end 214 coupled or connected to inner structure 208 and distal end 216 coupled or connected to outer structure 210.

Optic 202 may be molded directly onto haptic 204. Alternatively, optic 202 may be formed or fabricated separately from haptic 204, and then attached to haptic 204. In certain embodiments, haptic 204 is first machined or molded, and then optic 202 is molded and/or machined over or on top of haptic 204.

Optic 202 is preferably made from a relatively soft material, so that it can deform or change shape readily under the limited deforming forces produced by the capsular bag and/or ciliary muscle. An exemplary material is a relatively soft silicone material, although other suitable materials may be used as well. The stiffness of optic 202 may be less than 500 kPa, preferably from 0.5 kPa to 500 kPa. In some embodiments, the stiffness of optic 202 is between 25 kPa and 200 kPa or between 25 kPa and 50 kPa.

In contrast with optic 202, at least portions of haptic 204 (e.g., arms 212) are generally made of a relatively stiffer material than optic 202 material, so that haptic 204 can efficiently transmit ocular forces to optic 202. An exemplary material is a relatively stiff silicone material, although other suitable materials may be used as well, such as acrylic, polystyrene, or clear polyurethanes. The stiffness of haptic 204 may be greater than or equal to 500 kPa, or greater than or equal to 3000 kPa.

Arms 212 protrude or extend into optic 202 that include the clear aperture of optic 202. As used herein, the term "clear aperture" means the area of a lens or optic that restricts the extent of a bundle of rays from a collimated source or a distant light source that can imaged or focused by the lens or optic. The clear aperture is usually circular and is specified by its diameter. In some embodiments, the clear aperture has the same or substantially the same diameter as the optic. Alternatively, the diameter of the clear aperture may be smaller than the diameter of the optic, for example, due to the presence of a glare or PCO reducing structure disposed about a peripheral region of the optic.

Since inner structure 208 and the proximal ends 214 of arms 212 are located inside optic 202 and within the clear aperture thereof, at least these portions of haptic 204 are beneficially transparent or nearly transparent, so that it does not substantially block or scatter any light transmitted through optic 202. In addition, these portions of haptic 204 may have a refractive index that matches the refractive of optic 202 material so that interfaces between optic 202 and haptic 204 do not produce significant reflections or refractions that might produce scattered light within the eye, which might appear as a glare or haze to the patient.

A numerical example may be used to illustrate the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.202 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that haptic 204 and optic 202 may have any suitable refractive index.

Thus, the refractive indices of optic 202 and at least portions of haptic 204 inside optic 202 are equal or essentially the same. For the purposes of this document, "essentially the same" means that their refractive indices are equal to each other at a wavelength within the visible spectrum (i.e., between 400 nm and 700 nm). Note that haptic 204 and optic 202 may optionally have different dispersions, where the refractive index variation, as a function of wavelength, may be different for the haptic and the optic. In other words, if the refractive indices of haptic 204 and optic 202 are plotted as a function of wavelength, they may or may not have different slopes, and if the two curves cross at one or more wavelengths between 400 nm and 700 nm, then the refractive indices may be considered to be essentially the same or essentially equal.

The extension of arms 212 into optic 202 generally allows more effective transfer of radial forces along arms 212 to optic 202, since the inner diameter of inner structure 208 is less than the overall or outer diameter of optic 202. The relatively small "active area" of optic 202 located inside inner structure 208 allows ocular forces to be distributed over a smaller peripheral zone about the active area than if the same force were distributed over a periphery of the outer diameter, or a larger diameter, of optic 202. Since ocular forces are effectively concentrated over a relatively small area in the illustrated embodiment, this increases the pressure near the center of optic 202, which in turn increase the amount of curvature change or optical power change induced for a given amount of radial force on outer structure 210 and arms 212. As a result, the limited ciliary muscle or capsular bag force may produce a greater accommodative power change and/or axial translation optic 202. As used herein the term "active area" of an optic means a pupil of an optic over which a clinically significant change in optical power occurs in reaction to an ocular force generally sufficient to produce near vision in a human eye (e.g., an ocular force of 10 grams force).

The inner diameter of inner structure 208 is generally selected to be at least large enough that the active area of optic 202 can provide a change in optical power under scotopic lighting conditions (e.g., with a pupil diameter of the eye of 2 millimeters to 3 millimeters). For example, when intraocular lens 200 is used in a human eye, the active area is generally sufficiently large when the inner diameter of inner structure 208 is between 2 millimeters and 4 millimeters, or between 2.5 millimeters and 3.5 millimeters, or 3 millimeters plus or minus 0.25 millimeters.

In some embodiments, the axial thickness of inner structure 208 portion between arms 212, and/or overlapping proximal ends 214, is relatively large, for example, to help distribute more radial force on outer structure 210 into forces that change the shape of the anterior and posterior surfaces of optic 202. In some embodiments, the ratio of the optic center thickness to the axial thickness of inner structure 208 is less than or equal to 2. In other embodiments, greater accommodative power change in optic 202 is provided when the ratio of the optic center thickness to the axial thickness of inner structure 208 is less than 1.8 or less than 1.5.

Inner structure 208 may be in the form of a continuous ring and may generally have a radial thickness that is from 0.1 millimeters to 0.2 millimeters or of about 0.15 millimeters (e.g., 0.15 millimeters plus or minus 0.03 millimeters). While the continuous ring form of inner structure 208 favorably helps to maintain the figure of optic 202 when deformed during accommodation, it has been discovered that a relatively small radial thickness of inner structure 208 reduces the stiffness of inner structure 208, so that more of the radial forces transferred from arms 212 and are focused on changing the shape and accommodative optical power of optic 202. In some embodiments, outer structure 210 is broken at predetermined locations.

Figure 6:
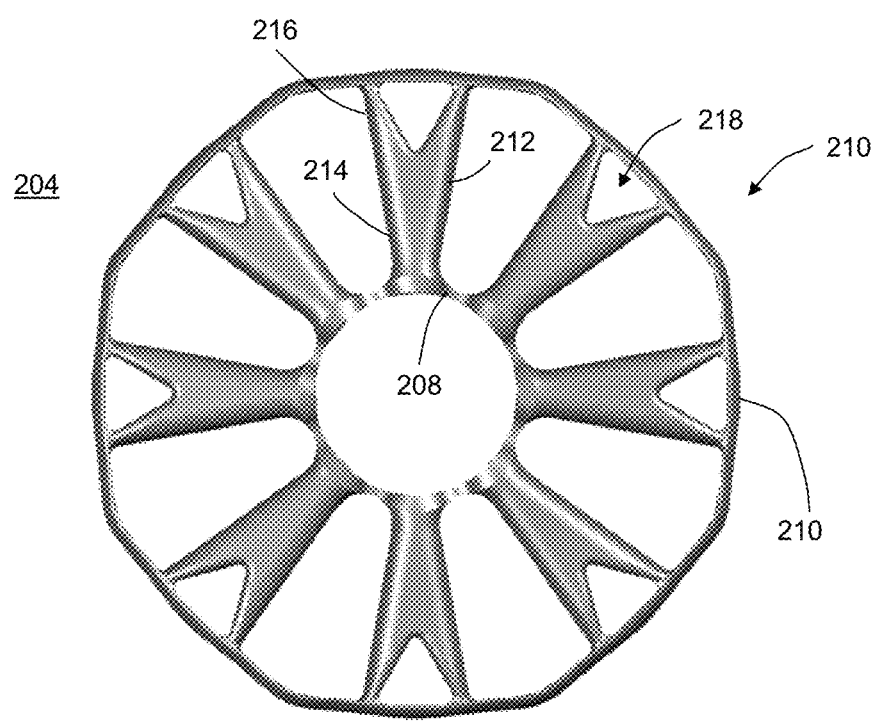
FIG. 6 is a top plan view of a haptic embodying features of this invention.
Figure 7:
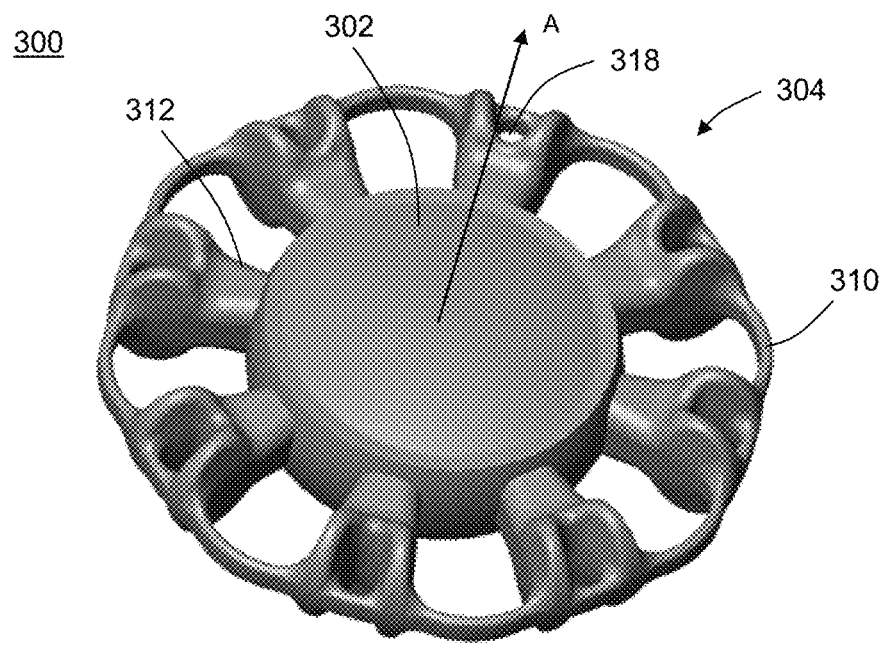
FIG. 7 is a perspective view of an intraocular lens embodying features of this invention.
Figure 8:
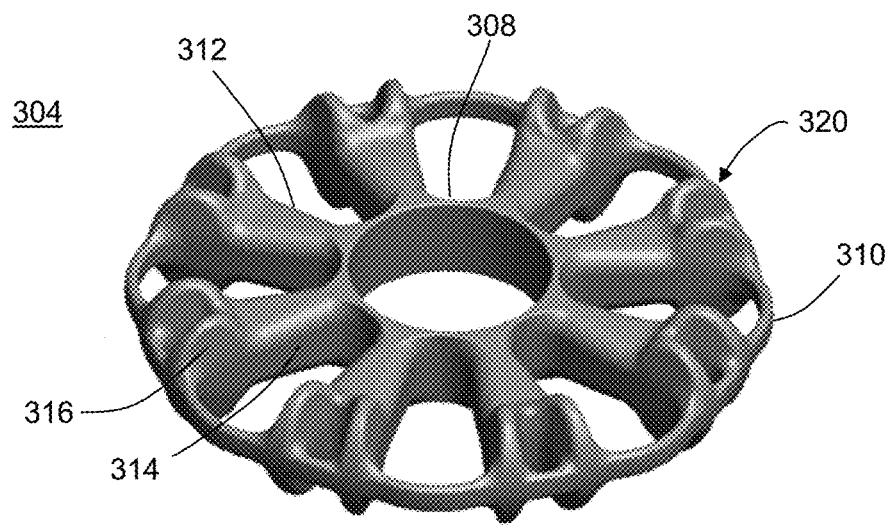
FIG. 8 is a perspective view of a haptic embodying features of this invention.
Figure 9:
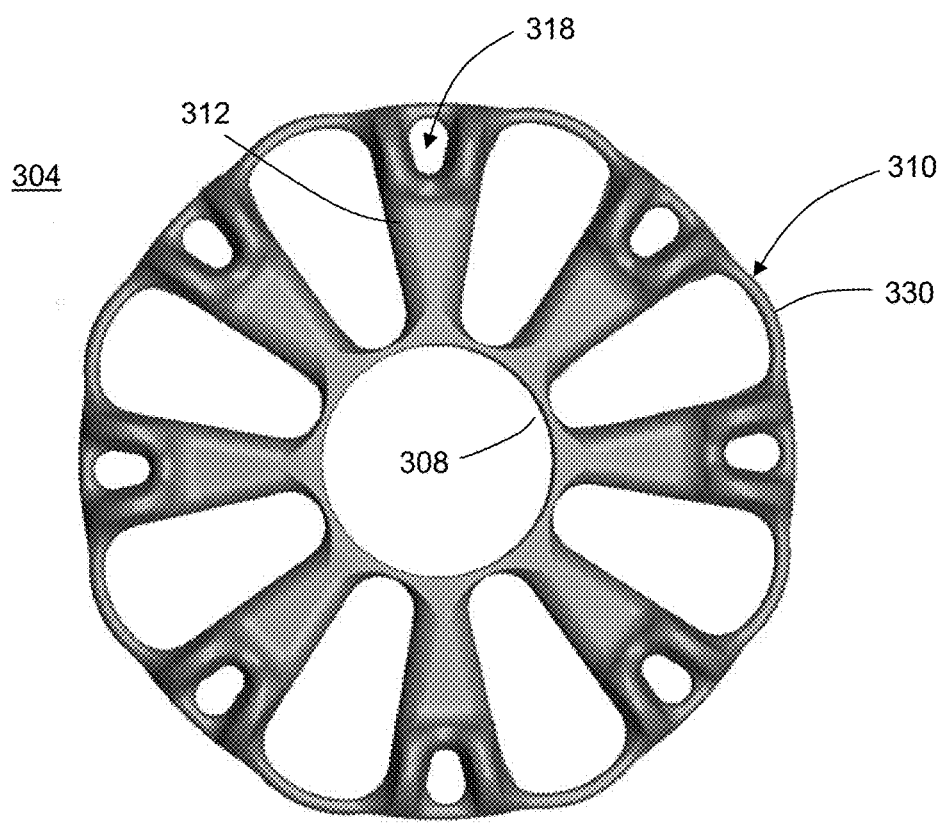
FIG. 9 is a perspective view of a haptic embodying features of this invention.

As seen in FIG. 6, arms 212 may be bifurcated or split at their distal ends 216 to form openings 218. Openings 218 may have a triangular shape, as shown in the illustrated embodiment. Alternatively openings 218 may have a different shape, for example, an oval shape (e.g., see. FIG. 9).

Opening 218 may be configured to reduce the mass of haptic 204, help direct radial forces toward inner structure 208, and/or control the shape of outer structure 210 during accommodation (e.g., help avoid bending or buckling). In some embodiments, some or all openings 218 are replaced regions of reduced axial thickness relative to a characteristic axial thickness of the remaining portions of arms 212. In other embodiments, outer structure 210 is either broken in the regions of openings 218 or has a reduced axial thickness relative to the axial thickness of the remaining portions of outer structure 210.

Outer structure 210 of haptic 204 mechanically couples intraocular lens 200 to capsular bag 20. Outer structure 210 may be in the form of a continuous ring and may generally have an axial thickness that is large enough to engage the equatorial region of capsular bag 20 over an area that is large enough to prevent tearing of the bag and to effectively couple ocular forces produced by capsular bag 20 to optic 202. In this regard, outer structure 210 may have an axial thickness that is from 0.5 millimeters to 1.0 millimeters or about 0.75 millimeters (e.g., 0.75 millimeters plus or minus 0.10 millimeters). In some embodiments, outer structure 210 has a radial thickness that is from 0.1 millimeters to 0.2 millimeters or about 0.15 millimeters (e.g., 0.15 millimeters plus or minus 0.03 millimeters). While the continuous ring form of outer structure 210 favorably helps to prevent buckling of AIOL 200, it has been discovered that a relatively small radial thickness reduces the stiffness of outer structure 210 so that radial forces are more effectively transferred along arms 212 and into the active area of optic 202.

Figure 5:
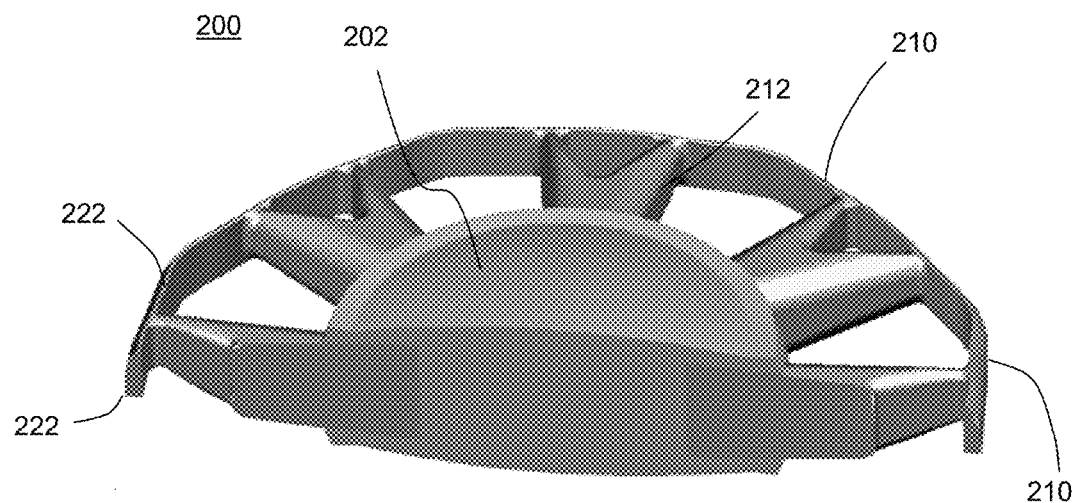
FIG. 5 is a cross sectional view of an intraocular lens embodying features of this invention.

Referring to FIG. 5, at least one of the edges of outer structure may have a discontinuity or sharp edge corner 222, for example, to help prevent PCO. Generally, sharp edge corner 222 has a radius that is less than 500 nanometers, preferably less than 200 nanometers. Additionally or alternatively, the side wall of optic 202 intersects the anterior face or posterior face of optic 202 to form a discontinuity or sharp edge corner that generally has a radius of curvature that is less than 500 nanometers, preferably less than 200 nanometers.

Outer structure 210 may be configured to have two outer diameters D1, D2, where D2 is greater than D1. In the illustrated embodiment, D1 is the outer diameter of outer structure 210 along opposite pairs of arms 212, while D2 is the outer diameter of outer structure 210 between adjacent pairs of arms 212. D1, D2 are advantageously selected to allow the AIOL 200 to accommodate a range of capsular bag sizes that is generally superior to a substantially equivalent outer structure that is circular or even oval in shape, or that includes indents that protrude inwardly toward the center of the intraocular lens. For example, the larger diameter D2 provides for at least portions of a capsular bag having a diameter of, or about equal to, D2 to contact the outer structure 210 when the eye is in a disaccommodative state, whereby accommodative forces may be effectively transmitted to optic 202. Alternatively, if the capsular bag has a diameter of, or about equal to, D1, then the capsular bag will contact the outer structure about its entire circumference. The capsular bag may be slightly taut over portions of ring 202 having the diameter D2, but the overall stress on the capsular bag is less than that experienced for a ring having a constant outer diameter of D2. Accordingly, the outer structure 210 of AIOL 200 is favorably configured to accommodate a larger variation of bag sizes than a substantially equivalent intraocular lens having an outer structure with a constant outer diameter. In certain embodiments, the outer diameter D2 is between 20 microns and 500 microns greater than the outer diameter D1, preferably between 40 microns and 250 microns greater than the outer diameter D1.

In certain embodiments, optic 202 is a multifocal optic, changes from a monofocal optic to a multifocal optic, depending upon the amount of ocular force on haptic 204 and/or the state of accommodation of the eye into which AIOL 200 is inserted.

Referring to FIGS. 7-11, an AIOL 300 according to an embodiment of the present invention is shown that comprises an optic 302 and a haptic or support structure 304 configured to effectively transfer an ocular force from a human or animal eye to optic 302 so as to produce a range of powers in response to an ocular force. Haptic 304 includes an inner structure 308 and an outer structure 310 and a plurality of arms 312 connecting or coupling structures 308, 310 to one another so as to efficiently and effectively transfer the ocular force to changing the shape and/or axial location of optic 302, thereby providing a change in optic power and/or focal plane location of optic 302. Arms 312 each include a proximal end 314 coupled or connected to inner structure 308 and distal end 316 coupled or connected to outer structure 310.

AIOL 300 is similar to AIOL 200 in many ways; however, also includes design features that are configured alter the way in which forces are transferred from haptic 304 to optic 302, or to otherwise alter performance and/or function. Where appropriate, structures and features of AIOL 200 discussed above may be incorporated into AIOL 300. For example, AIOL 300 may be made of the same or similar materials as those discussed for AIOL 200. Except where indicated otherwise, dimensions of AIOL 200 may be incorporated into embodiments according to AIOL 300 (e.g., the thickness or other dimensions of inner structure 308 may be the same or similar to those illustrated and discussed for inner structure 208; the shape and/or size of at least portions of arms 312 may be the same or similar to those illustrated and discussed for arms 212; and the like).

Arms 312 have a general shape that is similar to that of arms 212 of haptic 202, for example, including a bifurcated distal ends 316. Outer structure 310 comprises a series of arcuate ribbons 330 connecting individual arms 312 to one another. In the illustrated embodiment, ribbons 330 curve outwardly away from optical axis OA, so that portions of ribbons 330 between arms 312 are disposed at a greater radial distance from optical axis OA than portions of ribbons 330 that are coupled or connected to arms 312. Distal ends 316 of arms 312 generally bulge axially compared to the proximal end 314. Distal ends 316 of arms 312 are also curvaceous and void of sharp edges or discontinuities. In order to reduce PCO, the anterior and posterior faces of optic 302 contain sharp edges, similar or equal to those described above with regard to optic 202.

Figure 10:
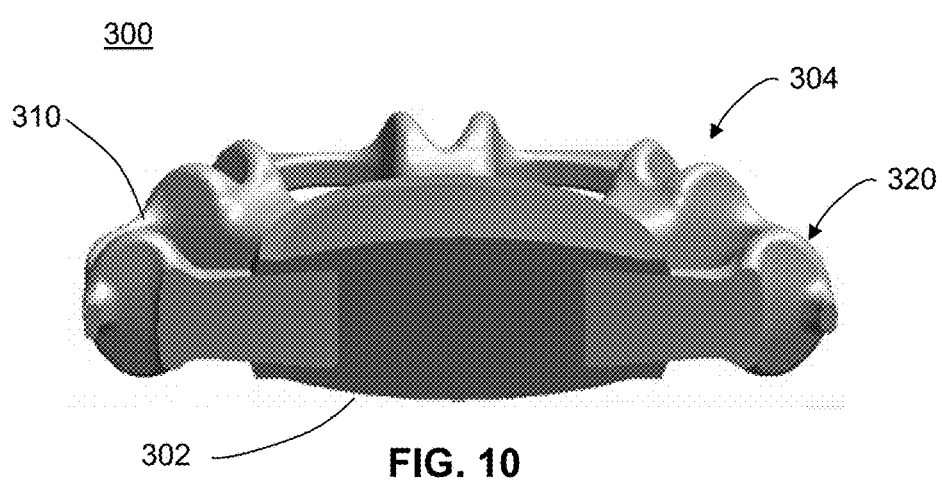
FIG. 10 is a cross sectional view of an intraocular lens embodying features of this invention.
Figure 11:
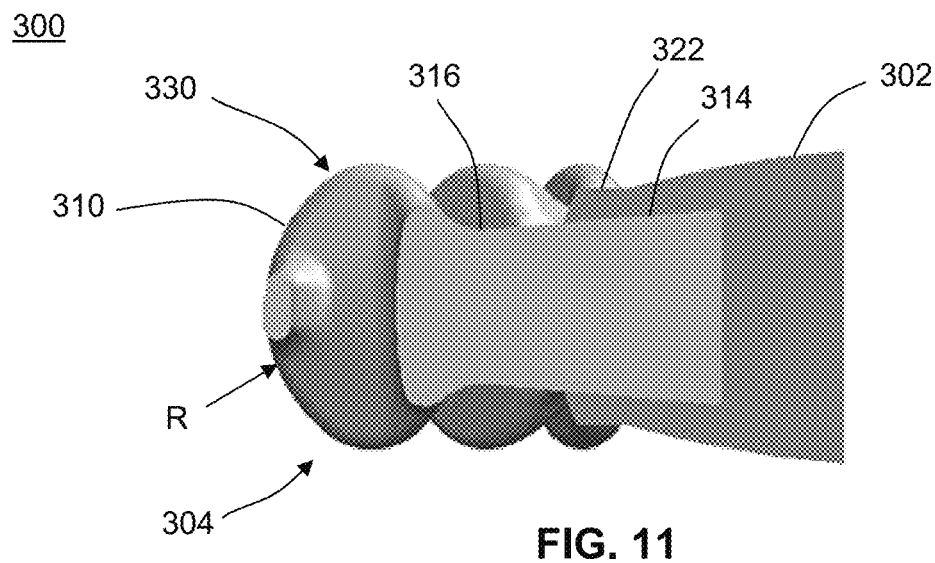
FIG. 11 is a cross sectional view of a portion of an intraocular lens embodying features of this invention.

Referring to FIGS. 10 and 11, outer structure 310 notably has a peripheral region 320 that is generally arcuate in cross-section, for example, to engage a larger portion of the capsular bag than outer structure 210 of AIOL 200. In some embodiments, outer structure 310 has an axial thickness in the vicinity of peripheral region 320 that is from 1.8 millimeters to 2.2 millimeters or about 2.0 millimeters (e.g., 2 millimeters plus or minus 0.1 millimeters). It has been discovered that the relatively large axial thickness of peripheral region 320 (or, large axial extent measured as the distance of the portion of the arm along an axis that is normal to the optical axis) is effective in transferring much of the forces produced by capsular bag 20 and/or zonules 24, since capsular bag 20 is engaged over a large axial extent. Thus, outer structure 310 engages a large extent or area of capsular bag 20, while also providing skeletal structure with a relatively low mass. The low mass of outer structure 310 results in a relatively low stiffness, thus allowing it to conform to changes in the shape of capsular bag 20 during accommodation. This, in turn, allows more of the forces produced by the changing shape of capsular bag 20 to be coupled into haptic 304 and transferred into changing the shape and optical power of optic 302.

Peripheral region 320 has an arcuate shape in a plane parallel to, and passing through, the optical axis OA that is convex. The arcuate shape is characterized by a radius of curvature R. In certain embodiments, radius of curvature R is equal to a radius of curvature of an average capsular bag of a population. For example, radius of curvature R may be 1.13 millimeters plus or minus 0.02 millimeters. In certain embodiments, radius of curvature R is greater than a radius of curvature of an average capsular bag of a population. For example, radius of curvature R may be 1.16 millimeters plus or minus 0.02 millimeters or greater than 1.16 millimeters. A radius of curvature of a peripheral region of haptic 204 may be similarly configured.

Referring to FIG. 11, in some embodiments, the relatively thick optic 302 (or optic 202 of IOL 200) comprises a peripheral region 322 that includes, in cross section, a counter taper that is configured to reduce glare from light incident on optic 302. The counter taper may have an angle from the horizontal plane that is from −3 degrees to −7 degrees. Thus, the angle formed in cross section at the juncture of peripheral region 322 and other portions of the adjacent optic 302 surface is less than 180 degrees.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An intraocular lens, comprising:
    an optic disposed about an optical axis including an anterior surface and a posterior surface defining a clear aperture of the optic; and
    a haptic attached to the optic, comprising:
        an inner structure circumferentially disposed about the optical axis;
        a plurality of arms having a proximal portion coupled to the inner structure and a distal portion extending away from the inner structure, wherein the plurality of arms are connected together via a series of arcuate ribbons, wherein each ribbon extends between each pair of adjacent arms at the distal portion, and further wherein each ribbon is curved outwardly away from the optic axis such that a portion of each ribbon between each pair of adjacent arms is disposed at a greater radial distance from the optical axis than a portion of the ribbon coupled to an arm;
        wherein the distal portion of each arm has a larger axial extent than an axial extent of the proximal portion of each arm.

2. The intraocular lens of claim 1, wherein the arms are bifurcated in a radial direction away from the proximal portion.

3. The intraocular lens of claim 1, wherein the inner structure and at least a portion of the arms are disposed inside the optic.

4. An intraocular lens, comprising:
   an optic disposed about an optical axis including an anterior surface and a posterior surface defining a clear aperture of the optic; and
   a haptic, attached to the optic, comprising:
      an inner structure circumferentially disposed about the optical axis; and
      a plurality of arms having a proximal portion adjacent to the inner structure and a distal portion extending away from the inner structure, wherein the plurality of arms are connected together via a series of arcuate ribbons, wherein each ribbon extends between each pair of adjacent arms at the distal portion, and further wherein each ribbon is curved outwardly away from the optic axis such that a portion of each ribbon between each pair of adjacent arms is disposed at a greater radial distance from the optical axis than a portion of the ribbon coupled to an arm;
   wherein the distal portion of each arm has a larger axial extent than an axial extent of the proximal portion of each arm.

5. The intraocular lens of claim 4, wherein the inner structure is continuous about the optical axis and is configured to maximize the transfer of deforming force from the arms to the optic.

6. The intraocular lens of claim 4, wherein the arms are bifurcated in a radial direction away from the proximal portion.

* * * * *